(12) United States Patent
Dimarco et al.

(10) Patent No.: US 6,938,203 B1
(45) Date of Patent: Aug. 30, 2005

(54) METHOD AND APPARATUS FOR AUTHORING OF CUSTOMIZABLE MULTIMEDIA DOCUMENTS

(76) Inventors: Chrysanne Dimarco, 133 Geoffrey Street, Toronto, Ontario (CA) M6H 1P4; Mary Ellen Foster, 5883 Inglis Street, Halifax, Nova Scotia (CA) B3H 1K7

(*) Notice: Subject to any disclaimer, the term of this patent is extended or adjusted under 35 U.S.C. 154(b) by 0 days.

(21) Appl. No.: 09/502,233

(22) Filed: Feb. 11, 2000

Related U.S. Application Data

(63) Continuation of application No. PCT/CA98/00771, filed on Aug. 11, 1998.

(30) Foreign Application Priority Data

| Aug. 11, 1997 | (GB) | ................................. 9716986 |
| Sep. 22, 1997 | (GB) | ................................. 9720133 |
| Feb. 24, 1998 | (CA) | ................................. 2230367 |

(51) Int. Cl.[7] ............... G06F 17/00; G06F 17/60

(52) U.S. Cl. ............ 715/513; 715/511; 715/907; 705/3

(58) Field of Search .................. 715/513, 514, 715/511, 907; 705/3; 707/7, 100

(56) References Cited

U.S. PATENT DOCUMENTS

| 5,207,580 A * | 5/1993 | Strecher ............... 434/238 |
| 5,951,300 A * | 9/1999 | Brown ................. 434/236 |
| 6,434,531 B1 * | 8/2002 | Lancelot et al. ........ 705/3 |
| 6,684,188 B1 * | 1/2004 | Mitchell et al. ........ 705/3 |
| 2004/0205656 A1 * | 10/2004 | Reulein et al. ........ 715/530 |

OTHER PUBLICATIONS

DiMarco et al. "HealthDoc: Customizing patient information and health education by medical condition and personal characteristics. "Workshop on Artificial Intelligence in Patient Education, Glasgow, Aug. 1995 http://www.cs.toronto.edu/compling/Publication.*

C. DiMarco et al., "The automated generation of Web documents that are tailored for the reader", Proceedings of the 1997 AAAI Spring Symposium on Natural Language Processing for the World Wide Web, Mar. 1997, pp. 44-53, XP002086363, Stanford University, Palo Alto, CA, US.

G. Hirst et al., "Authoring and Generating Health-Education Documents That Are Tailored to the Needs of the Individual Patient", User Modeling: Proceedings of the Sixth International Conference UM97, Jun. 1997, p. 107-118, XP002086454, Sardinia, IT.

E.H. Hovy, "A New Level of Language Generation Technology: Capabilities and Possibilities", IEEE Expert, vol. 7 No. 2, Apr. 1992, pp. 12-17, XP000331536, Los Alamitos, CA, US.

(Continued)

*Primary Examiner*—Stephen Hong
*Assistant Examiner*—Adam L. Basehoar
(74) *Attorney, Agent, or Firm*—John Orange; Santosh Chari; Sean Zhang

(57) ABSTRACT

A method and apparatus for generating customizable documents comprising a datafile including a data structure for defining relationships between elements of a document and variations thereof. A parser for reading the datafile and for creating instances of document-class data structures in accordance with general document class definitions. A user interface for inputting purpose parameters specifying a document variation and a selection engine for utilizing the current values of the purpose parameters for generating customized versions of the document.

12 Claims, 8 Drawing Sheets

OTHER PUBLICATIONS

C. DiMarco et al., "Generation by selection and repair as a method for adapting text for the individual reader", Proceedings of the Workshop on Flexible Hypertext, Eighth ACM International Hypertext Conference, Apr. 1997, Southampton UK.

E. Hovy et al., "Managing sentence planning requirements", Proceedings of the ECAJ-96 Workshop: New Directions in Planning and Natural Language Generation, Aug. 1996, Budapest.

E. Hovy et al., "The HealthDoc sentence planner", Proceedings of the 8th International Workshop on Natural Language Generation, Jun. 1996, Brighton.

C. DiMarco et al., "Customizing patient information and health education by medical condition and personal characteristics", First International Workshop on Artificial Intelligence in Patient Education, Aug. 1995, Glasgow.

* cited by examiner

Block 1—The parameters:

```
PurposeParameters
    (<feature 1>=<list of possible values>)&
    (<feature 2=<list of possible values>)&
    [Subsequent lines define remaining features]

RepresentationLevelParameters
    (<list of representation levels to output>)
```

Block 2—Identification of the top-level object:

```
toplevel=Document.<name of main Document>
```

Block 3—Definitions of all Documents and their variations:

Sub-block: Definition of a Document and its variations.

Field: Definition of the Document.

```
Document <name of document>
|variations=<list of variations of the document>&
annotations=<list of annotations>|
```

Field: Definitions of the Document's variations.

Subfield: Definition of a variation of the Document.

```
DocumentVariation <name of document variation>
|condition=<Boolean expression>&
componentList=<list of components of the document variation>&
annotations=<list of annotations>|
```

Subsequent subfields define remaining variations of the Document.

Subsequent sub-blocks define remaining Documents and their variations.

Block 4—Definitions of all Sections and their variations:

Sub-block: Definition of a Section and its variations.

Field: Definition of the Section.

```
Section <name of section>
|variations=<list of variations of the section>&
annotations=<list of annotations>|
```

Field: Definitions of the Section's variations.

Subfield: Definition of a variation of the Section.

```
SectionVariation <name of section variation>
|condition=<Boolean expression>&
componentList=<list of components of the section variation>&
annotations=<list of annotations>|
```

Subsequent subfields define remaining variations of the Section.

Subsequent sub-blocks define remaining Sections and their variations.

FIGURE 2(a)

Block 5—Definitions of all Topics and their variations:

Sub-block: Definition of a Topic and its variations.

Field: Definition of the Topic.
```
Topic <name of topic>
|variations=<list of variations of the topic>&
annotations=<list of annotations>|
```
        Field: Definitions of the Topic's variations.

Subfield: Definition of a variation of the Topic.
```
TopicVariation <name of topic variation>
|condition=<Boolean expression>&
componentList=<list of components of the topic variation>&
annotations=<list of annotations>|
```
    Subsequent subfields define remaining variations of the Topic.

Subsequent sub-blocks define remaining Topics and their variations.

Block 6—Definitions of all Sentences and their variations:

Sub-block: Definition of a Sentence and its variations.

Field: Definition of the Sentence.
```
Sentence <name of sentence>
|variations=<list of variations of sentence>&
annotations=<list of annotations>|
```
        Field: Definitions of the Sentence's variations.

Subfield: Definition of a variation of the Sentence.
```
SentenceVariation <name of sentence variation>
|condition=<Boolean expression>&
componentList=<list of components>&.
levelList=<list of representation levels>&
annotations=<list of annotations>|
```
            Subfield: Definitions of the Sentence's representations.
```
SentenceRepLevel <name>
|repLevel=<list of representation levels>&
componentList=<a string or list of components>&
annotations=<list of annotations>|
```
    Subsequent subfields define remaining variations of the Sentence and their representations.

Subsequent sub-blocks define remaining Sentences and their variations.

FIGURE 2(b)

Block 7—Definitions of all Lexicals and their variations:

Sub-block: Definition of a Lexical and its variations.

Field: Definition of the Lexical.

```
Lexical <name of lexical item>
|variations=<list of variations of lexical item>&
annotations=<list of annotations>|
```

Field: Definitions of the Lexical's variations.

Subfield: Definition of a variation of the Lexical.

```
LexicalVariation <name of lexical variation>
|condition=<Boolean expression>&
string=<character string>&
value=<DocumentClass>.<objectName>&
annotations=<list of annotations>|
```

Subsequent subfields define remaining variations of the Lexical.

Subsequent sub-blocks define remaining Lexicals and their variations.

Block 8—Definitions of all Words:

Field: Definition of a Word.

```
Word <word>
|value="<word>"|
```

Subsequent fields define remaining Words.

FIGURE 2(c)

```
Annotation <name of the Annotation object>
   |<property>="<value>"&
   <property>="<value>"&
   <Subsequent lines define remaining properties and their values>&
   parent=<name of the immediate ancestor of this Annotation object>|
```

FIGURE 3(a)

```
External <name of the External object>
  |fileName="<file name>"&
   profile=<list of parameters describing current user/audience>|
```

FIGURE 3(b)

METHOD AND APPARATUS FOR AUTHORING OF CUSTOMIZABLE MULTIMEDIA DOCUMENTS

This is a continuation of PCT/CA98/00771 filed Aug. 11, 1998.

This invention relates to a method and apparatus for the authoring of customizable multimedia documents and the adaptive generation of versions thereof for particular uses.

BACKGROUND OF THE INVENTION

Natural Language Generation (NLG) is a young but growing research field, whose goal is to build computer systems that automatically produce fluent and effective texts in various human languages. Generally, NLG systems have used knowledge databases containing general world knowledge and specific domain knowledge, together with various linguistic resources (e.g., lexicons, grammars, discourse relations), to produce texts with limited variation in word choice, sentence and discourse structure, and virtually no variation in rhetorical style or pragmatic purpose.

While various computational systems have been devised as solutions to the problem of producing documents with limited expressiveness in form and effect, none has presented a general solution to the problem of representing the kinds of knowledge that are needed to produce documents tailored to a specific use or audience in a manner that is systematic and extensible, and that further provides for the authoring of such documents by a non-computer-programmer professional writer. In addition, no system has yet presented a general solution for automatically integrating various aspects of document design (e.g., text, graphics, and presentation layout) into a single consistent representation format for use within a document intended for customization.

It is well-known from studies in communication that presentation of information in a manner that is tailored to the characteristics of a particular audience can be significant both in maintaining the interest of the members of the audience and in effectively conveying the meaning of the information. For example, in the health care industry, it has been shown that information that is tailored to the characteristics of an individual patient can have a far greater effect in producing compliance with suggested medical regimens as compared to generic information. (Stretcher et al 1994 have done pioneering work in this area).

But as Strecher et al's behavioural studies also showed, a sizeable number of different medical and personality factors had to be taken into account in producing customized health information that would have the desired effect on the intended patient. DiMarco et al (1995) noted that this kind of customization involves much more than producing each brochure or leaflet in half a dozen different versions for different audiences. Rather, the number of different combinations could easily be in the tens of thousands. While not all distinct combinations might need distinct customizations, it is nonetheless impossible in general to produce and distribute, in advance of need, the large number of different editions of each publication that is required for individual tailoring of information.

Thus there is a need for a computer system for the automated production of customized material that would tailor a general-purpose "master document" for a particular purpose or individual on demand. It must also be remembered that in the present context the term "document" is broadly used to define any textual or non-textual data, including multimedia and hypertext, having inter-relationships between the data, and that may be displayable or presented to a human audience in one of many presentations and formats.

As a further example, a master document may refer to the complete superset of instructions to direct the actions of a robot on an assembly line. In this instance, there exists a need to tailor or adaptively generate subsets of combinations of instructions for specific robot applications. Whether the master document is to be customized for a particular purpose, as in the robot example, or tailored for a specific audience, as in the case of health information, this process of adaptive document generation should be easily implementable on a computer system at minimum possible cost and maximum possible ease of use to both the author of the master document and the user of the generation system.

In the field of natural processing, or, computational linguistics, various computer systems have been implemented which attempt to produce customized documents. In the simplest cases, simple mail-merge techniques are used which enable "personalized" documents to be generated by using hand-coded decision rules indicating what information is to be included for various tailoring situations. However, these techniques result in very inflexible, and often, awkwardly structured, and poorly cohesive texts. Other systems utilize schema-based techniques to select and organize the content data according to simple document-template structures. But these templates are either too general-purpose to provide anything more than very coarse-grained adaptation in the resulting customized texts or too specific to the application in question to be appropriate for general use in adaptive generation systems.

A number of projects have used more sophisticated techniques from NLG research to build adaptive generation systems for both written texts and hypertext documents. The IDAS project (Reiter, Melish, and Levine 1995) recognized the need to tailor both textual and non-textual information, including visual formatting, hypertext input, and graphics output. IDAS also tried to address the need for explicit authoring tools in the adaptive document generation process, but here the focus was on authoring at the knowledge-base level (i.e., at the level of a computer system's internal representation), while there still exists a need to provide an authoring tool that may be used by a non-computer-programmer professional writer who could compose the master document at the level of ordinary English, with additional markup as required (e.g., HTML markup to support an HTML presentation format for a resulting customized version of the document). IDAS relies mainly on canned texts and aims to provide the user with a means of navigating through the whole "hyperspace" of possible (canned) texts. There is however a need to provide for a much finer-grained degree of tailoring than the IDAS implementation.

While IDAS relies mainly on canned texts, other adaptive generation systems do use more-dynamic text generation: the Migraine system (Carenini, Mittal, and Moore 1994) uses an approach to text planning that adaptively selects and structures the information to be given to a particular reader. However, Migraine relies on a large number of context-sensitive and user-sensitive "text plans" (i.e., text schemas) so that its methods of tailoring must of necessity be very specific to its particular domain. The PEBA-II system (milosavljevic and Dale 1996) uses more-general text plans, as well as text templates, that it can choose from to adapt information to the individual reader, but the tailoring done is very specific, focussing on the user's familiarity with a topic. The PIGLET system (Cawsey, Binsted, and Jones 1995) also uses a combination of text plans and text templates, but its tailoring is also quite specific in nature, mainly concerned with emphasizing material that is relevant to a particular patient. The ILEX-0 system (Knott, Mellish, Oberlander, and O'Donnell 1996) is similar to the PIGLET model in its anticipation of all the possible texts that might be generated, but also includes annotations (e.g., a condition on a piece of canned text) to allow some local customization. However, very free and flexible use of annotations could lead to problems of repetitive text and inappropriate use of referring expressions in the resulting document, requiring textual repair.

None of the previous systems provide for a text-repair facility of the kind described by Hovy and Wanner (1996) and Wanner and Hovy (1996). The paradigm of adaptive document generation by "selection and repair", as introduced by DiMarco, Hirst, Wilkinson, and Wanner (1995), that is, selection of the relevant pieces of information from a master document, and then repair of any syntactic or stylistic problems in the resulting document by a text-repair facility, is central to the goals of a customizable document system. However, the system should be able to support either an adaptive generation system with full facilities for selecting and repairing texts, as described by DiMarco, Hirst, Wilkinson, and Wanner (1995) and Hirst, DiMarco, Hovy, and Parsons (1997), or a simpler version of the system, based on "generation by selection only", i.e., with no facilities for textual repair, an implementation of which (called "WebbeDoc") is described by DiMarco and Foster (1997).

In summary, an author of a customizable document needs to be able to describe the variations of a document, which may be both textual and non-textual, at various levels of the document structure, together with conditions for selecting each variation.

The author then needs a means of selecting all the appropriate variations for a particular purpose or audience, re-assembling the selected variations into a coherent document, and producing an appropriately customized version of the document, in potentially many different levels of representation (e.g., surface English, a deep syntactic or semantic representation for use in textual repair) and presentation formats (e.g. HTML, LaTeX).

None of the existing adaptive document generation systems has provided a generally applicable method and apparatus for describing all the different ways in which a document could be customized, or for providing for a non-computer-programmer author of a customizable document to specify the possible variations, or for selecting the appropriate variations and producing a customized version of a document.

SUMMARY OF THE INVENTION

It is therefore an object of this invention to provide a system which mitigates to some extent the above outlined disadvantages. Also, the methods used by the present invention are more general than those used in previous systems, allowing not only the potential inclusion of text plans and schemas, text templates, and canned text, but also the dynamic generation of text that can then be subjected to very fine-grained revision and tailoring by a text-repair facility.

This invention seeks to provide a computer system for customizing an initial master document containing information for a multiplicity of versions of the document intended for the different purposes or different users, for a specific purpose or for a specific user.

In accordance with this invention, there is provided a computer system for customizing an initial master document in accordance with a user-defined set of purpose parameters. In accordance with a further aspect of the invention there is provided a data structure (i.e., the customizable, "master", document) for specifying relationships between elements of the document and between elements of the document and their variations.

A master document will therefore contain all the information that the system might need to include in any particular customized version of the document, together with annotations giving the selection condition as to when each piece of information is relatively and other annotations giving linguistic and formatting information, including for multimedia elements of the document.

A further aspect of the invention provides for a method and apparatus for reading said data structure into a form implementable on a suitably programmed processor such that the implementation of the data structure can store both the form and content of a master document, i.e. all the elements of the document and their variations, and can also act as the process for selecting the relevant variations of the document, according to given values of input parameters specifying the intended purpose or intended user, and then generally the appropriately customized version of the document.

BRIEF DESCRIPTION OF THE DRAWINGS

A better understanding of the invention will be obtained by reference to the detailed description of a preferred embodiment below and in respect to the following drawings in which:

FIG. 2 shows a generalised form of a data structure for specifying a customizable, master, document according to an embodiment of the present invention;

FIG. 3(a) shows a generalised form of a data substructure for use within the main data structure for specifying linguistic or presentation format information for a component of the master document;

FIG. 3(b) shows a generalised form of a data substructure for use within the main data structure for specifying hypertext links to parts of the main data structure or to other data structures of the form as specified in FIG. 2 and provided in other source datafiles;

DETAILED DESCRIPTION OF A PREFERRED EMBODIMENT

Figure 1:
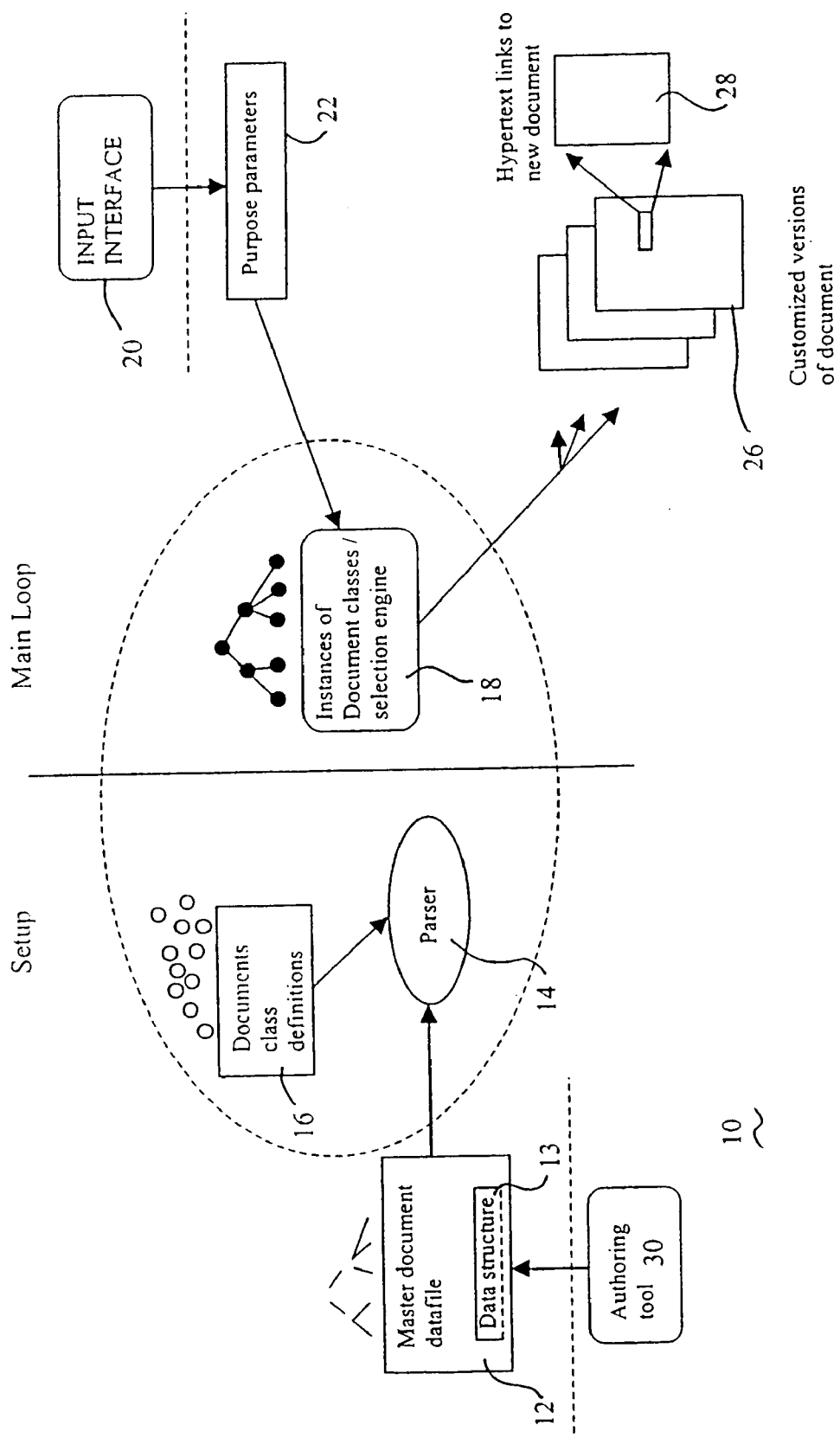
FIG. 1 is a schematic diagram showing the architecture of the system.

Referring to FIG. 1, an architecture of a customizable document system, the "tailoring engine", as shown generally by numeral 10. The system comprises: a datafile 12 including a data structure 13 for defining a master document; a parser 14 for reading in the contents of the datafile 12 and for creating instances of the document-class data structures 18 in accordance with the general definitions of document-class data structures 16; a user input interface 20 for reading new values of purpose parameters 22 which are joined by a selection engine 18. The selection engine 18 uses the current values of the purpose parameters to select the relevant variations of each component of the document and to generate appropriately customized versions 26 of a document, which may also include hypertext links to new documents 28, which may themselves be customizable documents of the form illustrated in FIG. 2.

The term "purpose parameter" as used herein means a parameter used in evaluating a selection condition associated with a particular variation of a document structure, where this parameter can be used in defining either a particular intended purpose or use of a customized version of the document or a particular intended user or audience for a customized version. These elements are explained in detail below.

Furthermore, the datafile may be generated by an authoring tool 30 in accordance with the detailed explanation below.

Referring to FIG. 2 an embodiment of the data structure 13 according to the present invention is described, which shows the blocks, sub-blocks, fields, and subfields of the data structure:

The data structure 13 has the following main blocks of information:
1. Identification of purpose parameters and representation-level parameters, and their possible values.
2. identification of toplevel object (i.e., the main Document).
3. Definitions of main Document and any subDocuments.
4. Definitions of Sections.
5. Definitions of Topics.
6. Definitions of Sentences.
7. Definitions of Lexicals.
8. Definitions of Words.
9. Definitions of Annotations (replaces previous 9. Definitions of Formats).
10. Definitions of External objects.

Each of these blocks of the data structure will now be described in turn.

Block 1: The purpose parameters. The first block of the data structure identifies the purpose parameters, or user parameters, together with their possible values, that can be used in forming the Boolean expressions that give the conditions for selecting each variation of a document.

The first block also identifies the representation-level parameters, together with their possible values, that can be used in forming the Boolean expressions that give the conditions for selecting each desired level of representation of the sentences in the master document during the process of generating a customized version of the document.

Block 2: The toplevel object. The toplevel object identifies the document-class instance which is the "root" element of the entire document. It is with this object that the resolution process for generating a customized version of the document begins.

Blocks 3–9: The program structures. Blocks 3–9 describe the program structures, the classes that implement the substructures of the data structure that specify the form and content of a customizable document. The program structures are related in the following manner:

A datafile describing a set of program structures is a particular example of a customizable document created for various uses. The datafile may be divided into various parts.

Firstly, the data structure may be divided into components, or elements, referred to as the classes Document, Section, Topic, Sentence, and Lexical, which each implement a substructure of the data structure that define a component of a customizable document. Each such substructure of the data structure also includes the variations of a component and the conditions for selecting the appropriate variation of a component.

In addition, the data structure contains basic components which are instances of the classes Word and Annotation, and other components, which are instances of the class External, for linking to other datafiles.

Block 3: The Documents.

In FIG. 2, Block 3 describes the instances of the class Document. Each Document description must specify the following properties:
  A list of its variations. Each variation must be an instance of the class DocumentVariation.
  A list of its annotations. Each annotation must be an instance of the class Annotation.

An instance of the class Annotation can specify both textual and non-textual properties of a document or a component of a document in terms of a particular document-layout format, structure, or linguistic representation. For example, an Annotation object could specify multimedia elements of the document's layout, such as alignment of text, font size, background colour, text colour, and graphics; other Annotation objects could specify linguistic information such as discourse relations or coreference links.

Each variation of a Document class is then described as an instance of the class DocumentVariation. Each DocumentVariation description specifies the following properties:
  The condition for selecting this variation. The condition must be a Boolean expression composed from pairs of purpose parameters and their allowable values.
  A list of the components of this variation. Each component must either be an instance of the class Document or an instance of the class Section.
  A list of annotations for this variation. Each annotation must be an instance of the class Annotation.

Block 4: The Sections. Block 4 describes the instances of the class Section. Each Section description specifies the following properties:
  A list of its variations. Each variation must be an instance of the class SectionVariation.
  A list of its annotations. Each annotation must be an instance of the class Annotation.

Each variation of a Section class is then described as an instance of the class SectionVariation. Each SectionVariation description specifies the following properties:
  The condition for selecting this variation. The condition must be a Boolean expression composed from pairs of purpose parameters and their allowable values.
  A list of the components of this variation. Each component must either be an instance of the class Section or an instance of the class Topic.
  A list of the annotations for this variation. Each annotation must be an instance of the class Annotation.

Block 5: The Topics. Block 5 describes the instances of the class Topic. Each Topic description specifies the following properties:
  A list of its variations. Each variation must be an instance of the class Topic-Variation.
  A list of its annotations. Each annotation must be an instance of the class Annotation.

Each variation of a Topic class is then described as an instance of the class TopicVariation. Each TopicVariation description specifies the following properties:

- The condition for selecting this variation. The condition must be a Boolean expression composed from pairs of purpose parameters and their allowable values.
- A list of the components of this variation. Each component must either be an instance of the class Topic or an instance of the class Sentence.
- A list of the annotations for this variation. Each annotation must be an instance of the class Annotation.

Block 6: The Sentences. Block 6 describes the instances of the class Sentence. Each Sentence description must specify the following properties:

- A list of its variations. Each variation must be an instance of the class SentenceVariation.
- A list of its annotations. Each annotation must be an instance of the class Annotation.

Each variation of a Sentence class is then described as an instance of the class Sentence-Variation. Each Sentence-Variation description must specify the following properties:

- The condition for selecting this variation. The condition must be a Boolean expression composed from pairs of purpose parameters and their allowable values.
- A list of the components of this variation.
- A list of the representations of this variation. Each representation must be an instance of the class SentenceRepLevel.
- A list of annotations for this variation. Each annotation must be an instance of the class Annotation.

Each SentenceRepLevel description must specify the following properties:

- The condition for selecting this sentence representation. The condition must be a list of one or more representation-level parameters.
- A list of the components of this variation. Each component must be an instance of the class Lexical.
- A list of the annotations for this variation. Each annotation must be an instance of the class Annotation.

In the current implementation of the system, an instance of the class SentenceRepLevel may be a character string, with any Lexical components identified by surrounding reserved characters. This is a simplification made for ease of testing system prototypes, and does not limit the scope of the invention.

Block 7: The Lexicals. Block 7 describes the instances of the class Lexical. Each Lexical description must specify the following property:

- A list of its variations. Each variation must be an instance of the class LexicalVariation.
- A list of its annotations. Each annotation must be an instance of the class Annotation.

Each variation of a Lexical class is then described as an instance of the class LexicalVariation. Each LexicalVariation description must specify the following properties:

- The condition for selecting this variation. The condition must be a Boolean expression composed from pairs of purpose parameters and their allowable values.
- A character string associated with this LexicalVariation instance.
- A list of annotations for this variation. Each annotation must be an instance of the class Annotation.

A single component, which may be an instance of any of the classes External, Word, Lexical, Sentence, Topic, Section, or Document. Each of these cases is dealt with as follows:

1. If a component is a Word, then it is treated as a simple string to be concatenated to the result returned.
2. If a component is a Lexical, then it is treated as a set of variations of a word, which will be resolved to select the appropriate version of the word. In this way, near-synonymy can be handled within the system.
3. If a component is a Sentence, Topic, or Section, then it is treated as a set of variations of a separate piece of a document, which will be resolved to select the appropriate version.
   In this way, adaptive hypertext can be handled within the system.
4. If a component is a Document, then it is treated as a whole complete document.
   In this way, hypertext links to other documents internal to the same datafile can be handled within the system.
5. If a component is an External object, then it is treated as a whole complete customizable document.
   In this way, hypertext links to other customizable documents can be handled within the system.

Block 8: The Words. Block 8 describes the instances of the class Word. Each Word description must specify its associated string and its associated annotations. Each annotation must be an instance of the class Annotation.

Block 9: The Annotations. Block 9 describes the instances of the class Annotation that will be used to insert all the relevant linguistic and forming information into the customized version of the document to be output. A description of block 9 is not included in FIG. 2. Instead, the general structure of an Annotation class object is shown in FIG. 3(a).

The Annotation objects can be grouped into several distinct sub-taxonomies, one for each type of linguistic or formatting annotations that will be attached to the main master-document data structure. For example, one Annotation sub-taxonomy might specify details of the HTML layout for the overall document and each component of the document; another Annotation sub-taxonomy might record properties of the discourse structure of the overall document and each component of the document, such as rhetorical relations and coreference links. Each Annotation object has a property "parent" to reference is immediate ancestor in its (sub-)taxonomy.

Block 10: The Externals. Block 10 describes the instances of the class External, which will be used to create hypertext links to other customizable documents specified in other datafiles.

Each External description must specify the following attributes:

- The name of the file containing the external customizable document.
- A user profile. The user profile is a list of parameters that describe the user or audience for whom the document customization is being performed.

The general structure of an External class object is shown in FIG. 3(b).

The data structure 13 according to the present invention allows an author to describe the structure of a customizable document (i.e., a master document). The data structure has a recursive and object-oriented form and can be implemented using an object-oriented programming language so that a customizable document described in the form of the data structure can be implemented as an object-oriented computer program.

The elements of the data structure are related by both part relationships and by inheritance relationships, so that the relationships between the elements of a customizable document described in the form of the data structure and implemented as a corresponding object-oriented computer program can be recognized and maintained by the object hierarchy and inheritance mechanism of an object-oriented computer program.

Moreover, an object-oriented computer program that implements the data structure is both the form and content of a customizable document and the process for selecting and generating an appropriately customized version of the document. Thus the data structure is generic in the sense that it can implement any cusotmizable document given in the form of the data structure.

The data structure 13 describes the corpus text of a specific cusotmizable document (i.e., a master document) having elements and structure, as shown in FIGS. 2(*a*), 2(*b*) and 2(*c*) following.

The form of the data structure is defined by the set of general class objects 16 describing the elements and structure of a customizable document in terms of object-oriented program structures. These class objects are related by both part relationships and by inheritance relationships to be explained below.

The operation of the system 10 (the "tailoring engine") may be explained as follows:

The parser program 14 reads in and parses the master-document datafile 12 to recognize its structure and then maps the contents of the input datafile into class objects of name according to class names specified in the input data structure. Properties of the classes are also recognized according to information contained in the data structure.

The parser program 14 also acts as a document-class instantiator program which uses the parsed contents of the input datafile to dynamically create instances of the program structures identified by the general class objects described above. Properties of the classes are also dynamically assigned according to information contained in the data structure.

An integration of data structures with the main process of the system comprises the following:

The instances of the class objects dynamically generated from the input datafile, which provide two simultaneous functions:
  1. The program data structures describing the elements, structure, and content of the master document.
  2. The selection process for generating the appropriate customized version of the document.

Thus, a feature of the system is that given the current values of the purpose parameters, the instances of the program data structures, that is to say, the instances of the class objects describing the elements of the master document, execute themselves to select and generate the appropriate customized version of the document.

The core of the system, that is, the integration of program data structures with the selection process, is generic in terms of the following parameters:

Application-independent. The system core is independent of the application: the only items that be re-defined for a new application are the input datafile and the interface for reading the current values of the purpose parameters. This is discussed further below.

Platform-independent. The system core is currently implemented in the Java programming language, so is platform-independent to the same extent as Java itself.

Processor-independent. The system core is currently implemented in the Java programming language, but is independent of the underlying programming language, i.e., processor, to the extent that the programming language used must provide an object-oriented paradigm and a semantics for property inheritance that is consistent with the specification of the resolution process used in the system for generating a customized version of a document from the instance of the program data structures.

Figure 5:
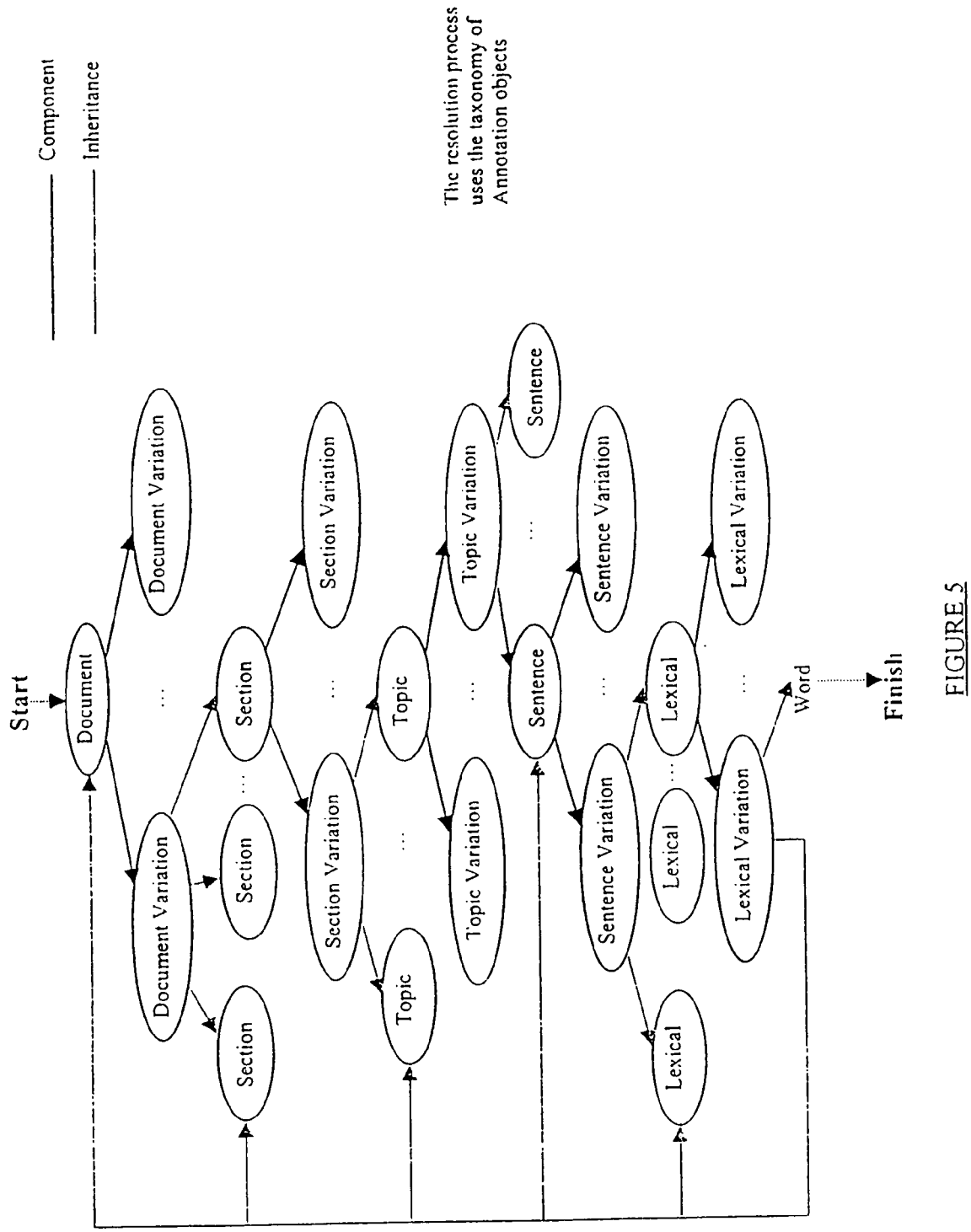
FIG. 5 is a graph showing the resolution process for a customized document generated according to an embodiment of the present invention.

The process of generating a customized version of a document from the instances of the program structures is referred to as resolution and will be discussed later with reference to FIG. 5.

A customized version of a document can be generated in any number of different levels of representation of its content (e.g., surface English; a syntactic or semantic representation to be used by a text-repair facility; and so on). The different representations to be generated for any given application must be indicated by the representation-level parameters in the description of the document given by the data structure in the input datafile. This information is specified in block 1 of the data structure as described with reference to FIGS. 2(*a*), 2(*b*), and 2(*c*) above.

Each different representation of the content of a customized version of the document will be generated along with a list of all the relevant annotations to the content. These annotations provide information on the multiple forms in which the document may subsequently be presented to a reader, and the linguistic information that may be used to guide subsequent repair of the customized document. The customized document that is generated will also include all annotations to the content concerning the External objects that can be used to provide hypertext links to other customizable documents or to other applications of the system 10 (the "tailoring engine") from FIG. 1.

Figure 4:
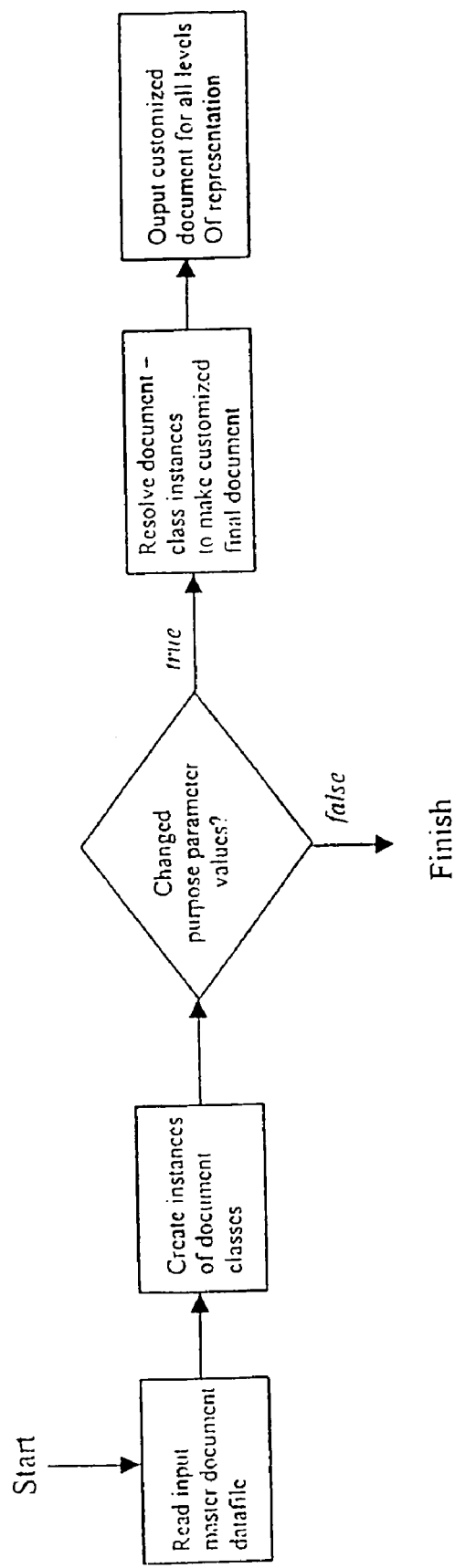
FIG. 4 is a flowchart of the overall process of reading-in as input the data structure and generating as output a final customized version of the document.

The process of generating a customized version of a master document is shown in FIG. 4. There are two main stages to this process, the initial setup and the main program loop. In the initial setup, the input datafile is read in and parsed, and the appropriate instances of the various document classes described above are created. The parser program 14 reads in the input datafile 12, which contains the data structure 13 giving the specification of a customizable document. As it reads in the file, the driver program also acts as a class instantiator to create instances of all relevant document classes according to the input data structure. Program links, i.e., references, are created between these class instances via the setting of their properties and assignment of their property values.

In each iteration of the main program loop, new values of the purpose parameters are read in, and a customized version of the document is generated as output for each specified level of representation. A user interface in the form of a reader program 20 obtains the new values of the purpose parameters. In the latter instance, the parameter values may be entered individually or may be read in from previously compiled profiles of user preferences stored in computer databases. This allows for the mass customization of information for high volumes of individual users with diverse characteristics, such as in the mass production of personalised financial investment advice.

A selection engine 18 resolves the document instances created in the setup stage according to the current values of the purpose parameters to generate the appropriately customized version of the document. The customized document is output in all specified levels of representation with all relevant linguistic and formatting information attached to each component of the document. If there are no more new purpose-parameter values to read in, the main program loop terminates.

The process of selecting the appropriate variation of each document structure is called "resolution". FIG. 5 is a graph showing the resolution process for a customized document generated according to an embodiment of the present invention. The pseudocode for the Resolve procedures, which implement the resolution process, is as follows:

Procedure: Resolve (for VariationContainer classes)
Parameters
(input)
   An instance of WorkingCondition
   (a list of purpose parameters and their current values)
(input)
   An instance of List
   (a list of the desired representation levels to output)
(output)
   An instance of DocumentObjectSet,
   i.e., a set of references to resolved DocumentObjects, with one set member for each desired level of representation of this VariationContainer instance
Algorithm:
if Resolve has already been called with this WorkingCondition then result is the previously saved result
call Satisfies on each variation of this Variation Container until the WorkingCondition is satisified.
call Resolve on this satisfying variation to return a DcoumentObjectSet
add the appropriate annotations for this VariationContainer into the returned DocumentObjectSet
end if
if no variation satisfies the WorkingCondition then result is null
else
result is the annotated DocumentObjectSet for this VariationContainer end if
Procedure: Resolve (for Variation classes)
Parameters:
(input)
   An instance of Working Condition
(input)
   An instance of List
   (a list of the desired representation levels to output)
(output)
   An instance of DocumentObjectSet,
   i.e., a set of references to resolved DocumentObjects, with one set member for each desired level of representation of this Variation instance
Algorithm:
create a new DocumentObjectSet for this Variation for each component of this Variation do
   call Resolve on the current component to return a DocumentObjectSet for this component
   add the appropriate annotations for this Variation into the returned DcoumentObjectSet
   attach the annotated DocumentObjectSet as a child of the DocumentObjectSet for this Variation end for
result is the annotated DocumentObjectSet for this Variation The "resolution" of the appropriate annotations for a given input data structure is handled as follows:

Each instance of a document class in the input data structure, down to the level of a Word instance, has an "annotations" property, which may be null, associated with it. This property is a list of all the Annotation objects that apply to this document-class instance and must contain one Annotation object for each of the distinct sub-taxonomies in the overall class of Annotation objects.

When a document-class instance is being resolved, its set of Annotation objects, as specified in its "annotations" property, will be collected and included in the content of the customized document.

In summary, an application system which wishes to put the invention into practice must execute the following steps:

1. An input datafile of the structure as described with reference to FIGS. 2(a), 2(b), and 2(c) is created;
2. A user interface in the form of a reader program to obtain new values of purpose parameters is provided. This reader program returns as output an instance of WorkingCondition which is a set of purpose parameters and their values (implemented as a hashtable in one embodiment of the invention).
3. The main program first reads in the datafile, then calls the reader program to obtain a new instance of WorkingCondition. The main program will then start the resolution process of the toplevel Document object by passing it the WorkingCondition.
4. The output of each iteration of the main program will be a customized version of the document in all the levels of representation specified in the input datafile using the representation-level parameters. Each representation of the customized document is output for possible later processing by the application system.

REFERENCES

Guiseppe Carenini, Vibhu O. Mittal, and Johanna D. Moore. "Generating patient-specific interactive natural language explanations." Proceedings, Eighteenth Annual Symposium on Computer Applications in medical Care, Washington D.C., November 1994, 5–9.

Alison Cawsey, Kim Binstead, and Ray Jones. "Personalised explanations for patient education." Proceedings of the Fifth European Workshop on Natural Language Generation, 1995, 59–74.

Chrysanne DiMarco and Mary Ellen Foster. "The automated generation of Web documents that are tailored to the individual reader." Proceedings of the 1997 AAAI Spring Symposium on Natural Language Processing for the World Wide Web, Standford University, March 1997.

Chrysanne DiMarco, Graeme Hirst, and Eduard Hovy. "Generation by selection and repair as a method for adapting text for the individual reader." Proceedings of the Workshop on Flexible Hypertext, Eighth ACM International Hypertext Conference, Southampton, UK, April 1997.

Chrysanne DiMarco, Graeme Hirst, Leo Wanner, and John Wilkinson. "HealthDoc: Customizing patient information and health education by medical condition and personal characteristics." Workshop on Artificial Intelligence in Patient Education, Glasgow, August 1995.

Graeme Hirst, Chrysanne DiMarco, Eduard Hovy, and Kimberly Parsons. "Authoring and generating health-education documents that are tailored to the needs of the individualpatient." In: Anthony Jameson, Cécile Paris, and Carlo Tasso (editors), *User Modeling: Proceedings of the Sixth International Conference, UM97* (Chia Laguna, Sardinia, Italy), Vienna and New York: Springer Wien New York, June 1997, 107–118.

Eduard Hovy and Leo Wanner. "Managing sentence planning requirements." Proceedings, ECAI-96 Workshop on Gaps and Bridges: New Directions in Planning and Natural Language Generation, Budapest, August 1996.

Alistair Knott, Chris Mellish, John Oberlander, and Mick O'Donnell. "Sources of flexibility in dynamic hypertext generation" Proceedings, Eighth International Natural Language Generation Workshop, Herstmonceaux Castle, June 1996, 151–160.

Maria Milosavljevic and Robert Dale. "Strategies for comparison in encyclopaedia descriptions." Proceedings, Eighth International Natural Language Generation Workshop, Herstmonceaux Castle, UK, June 1996, 161–170.

Ehud Reiter, Chris Mellish, and John Levine. "Automatic generation of technical documentation." Applied Artificial Intelligence, 9, 1995, 259–287.

Victor J. Strecher, Matthew Kreuter, Dirk-Jan Den Boer, Sarah Kobrin, Harm J. Hospers, and Cellette S. Skinner. "The effects of computer-tailored smoking cessation messages in family practice settings." *The Journal of Family Practice*, 39(3), September 1994, 262–270.

Leo Wanner and Eduard Hovy, "The HealthDoc sentence planner." Proceedings of the Eighth International Workshop on Natural Language Generation, Brighton, UK, June 1996.

Sample Data Structures

Selections from two sample data structures are presented in this section. The first example is for the customizable home page of the HealthDoc Project at the University of Waterloo (Waterloo, Canada). The second example is for a master document giving basic health information on diabetes.

Note that in the LexicalVariation labelled "lexDiabetesMaster-a" in Example 1, there is a link to another completely separate customizable document, contained in a different input datafile. This link is made through an instance of the External class.

EXAMPLE 1

A Customizable Web Page

//The parameters

PurposeParameters
|role=CLexpert physician layperson funder&
technical=high low&
age=senior adult child&
formality=formal informal&
coolness=cool bland|

RepresentationLevelParameters
|levels=english|

//The top-level object toplevel=Document.webbedoc

//The Documents and DocumentVariations

Document webbedoc
|title="The HealthDoc Project Home Page"&
variations=doc-a doc-b doc-c doc-d doc-e doc-f doc-g doc-h&
annotations=html-doc-webbedoc-toplevel|

DocumentVariation doc-a
|condition=(and coolness cool) (age adult) (role CLexpert)&
component List=Section.sec1 Section.sec2 Section.sec3 Section.sec4 Section.sec5 Section.sec6 Section.sec7&
annotations=html-doc-webbedoc-doc-a|

DocumentVariation doc-d
|condition=(and coolness bland) (age adult))&
componentList=Section.sec 1 Section.sec2 Section.sec3 Section.sec4 Section.sec 5 Section.sec6 Section.sec7&
annotations=html-doc-webbedoc-doc-d|

//The Sections and SectionVariations

Section sec1
|variations=sec 1 a sec 1 b sec 1 d sec 1 e sec 1 f
sec 1 g sec 1 h sec 1 i sec 1 j sec 1 k sec 1 l
sec 1 m sec 1 n sec 1 o sec 1 p sec 1 q sec 1 r&
annotations=html-sec-webbedoc-sec 1|

SectionVariation sec 1 a
|condition=
(and (role funder)(technical all)(coolness bland)(formality formal))&
componentList=Section.subsec1-1 Section.subsec1-2&
annotations=html-sec-webbedoc-sec1a|

Section subsec 1-1
|variations=subsec1-1 a&
annotations=html-sec-webbedoc-subsec1-1|

SectionVariation subsec 1-1a
|condition=( )&
componentList=Topic.topic1&
annotations=html-sec-webbedoc-subsec1-1|

Section sec2
|variations=sec2a sec2b&
annotations=html-sec-webbedoc-sec2|

Section subsec2-1
|variations=subsec2-1a&
annotations=html-sec-webbedoc-subsec2-1|
SectionVariation subsec2-1a
|condition=( )&
componentList=Topic.topic4  Topic.topic5 Topic.topic6 Topic.topic7&
annotations=html-sec-webbedoc-subsec2-1|
//The Topics and TopicVariations Topic topic4
|variations=topic4a&
annotations=html-topic-webbedoc-default|

TopicVariation topic4a
|condition=( )&
componentList=Sentence.sent4a-1 Sentence.sent4a-2&
annotations=html-topic-webbedoc-default|

Topic topic5
|variations=topic5a topic5b topic5c topic5d&
annotations=html-topic-webbedoc-default|
TopicVariation topic5a
|condition=(and (role physician)(technical high)&
componentList=Sentence.sent5a-1&
annotations=html-topic-webbedoc-default|

TopicVariation topic5c
|condition=(and (not (role physician))(technical high))&
componentList=Sentence.sent5c-1&
annotations=html-topic-webbedoc-default|

Topic topic7
  |variations=topic7a topic7b&
  annotations=html-topic-webbedoc-default|

TopicVariation topic7a
  |condition=(technical low)&
  componentList=Sentence.sent7a-1&
  annotations=html-topic-webbedoc-default|

TopicVariation topic7b
  |condition=(technical high)&
  componentList=Sentence.sent7b-1&
  annotations=html-topic-webbedoc-default|

Topic topic-compliance
  |variations=topic-compliance-a&
  annotations=html-topic-webbedoc-default|

TopicVariation topic-compliance-a
  |condition=( )&
  componentList=Sentence.sent-compliance-1 Sentence.sent-compliance-2 Sentence.sent-compliance-3 Sentence.sent-compliance-4&
  annotations=html-topic-webbedoc-default|

//The Sentences and Sentence Variations

Sentence sent4a-1
  |variations=sent4a-1i&
  annotations=html-sent-webbedoc-default|

SentenceVariation sent4a-1i
  |condition=( )&
  componentList=( )%
  levelList=SentenceRepLevel.sent4a-1i-english&
  annotations=html-sent-webbedoc-default|

SentenceRepLevel sent4a-1i-english
  |repLevel=english&
  componentList="Why do we want to be able to produce tailored documents?"&
  annotations=html-sent-webbedoc-default|

Sentence sent4-a2
  |variations=sent4a-2i&
  annotations=html-sent-webbedoc-default|

Sentence Variation sent4a-2i
  |condition=( )&
  componentList=( )&
  levelList=SentenceRepLevel.sent4a-2i-english&
  annotations=html-sent-webbedoc-default|

SentenceRepLevel sent4a-2i-english
  |repLevel=english&
  componentList="Because research in communication has shown that people pay more attention to messages that are aimed just at them."&
  annotations=html-sent-webbedoc-default|

Sentence sent5a-1
  |variations=sent5a-1i&
  annotations=html-sent-webbedoc-default|

SentenceVariation sent5a-1i
  |condition=( )&
  componentList=( )&
  levelList=SentenceRepLevel.sent5a-1i-english&
  annotations=html-sent-webbedoc-default|

SentenceRepLevel sent 5a-1i-english
  |repLevel=english&
  componentList="Studies have shown that health information that is tailored to a patient's specific medical condition and personal characteristics is much more effective than generic information in influencing ^lex Compliance^ and subsequent outcome."&
  annotations=html-sent-webbedoc-default|

Sentence sent7a-1
  |variations=sent7a-1i&
  annotations=html-sent-webbedoc-default|

SentenceVariation sent 7a-1i
  |condition=( )&
  componentList=( )%
  levelList=SentenceRepLevel.sent7a-1i-english&
  annotations=html-sent-webbedoc-default|

SentenceRepLevel sent7a-1i-english
  componentList="But it can be very difficult to write and keep track of many versions of the sample ^lexSynonymsl^."&
  annotations>html-sent-webbedoc-default|

Sentence sent8a-1
  |variations=sent8a-1i&
  annotations=html-sent-webbedoc-default|

SentenceVariation sent8a-1i
  |condition=( )&
  componentList=( )%
  levelList=SentenceRepLevel.sent8a-1i-english&
  annotations=html-sent-webbedoc-default|

SentenceRepLevel sent8a-1i-english
  |repLevel=english&
  componentList="What is needed is a computer system for the production of tailored health-information and patient-education documents, that would, on demand, customize a 'master document' to the needs of a particular individual."&
  annotations=html-sent-webbedoc-default|

Sentence sent8a-2
  |variations=sent8a-2i&
  annotations=html-sent-webbedoc-default|

SentenceVariation sent8a-2i
  |condition=( )&
  componentList=( )&
  levelList=SentenceRepLevel.sent8-2i-english&
  annotations=html-sent-webbedoc-default|

SentenceRepLevel sent8a-2i-english
  |repLevel=english&
  componentList="The HealthDoc project has currently built the first ^lexDiabetesMaster^ of such a system."&
  annotations=html-sent-webbedoc-default|

Sentence sent-compliance-1
  |variations=sent-compliance-1a&
  annotations=html-sent-webbedoc-default|

SentenceVariation sent-compliance-1a
  |condition=( )&
  componentList=( )&
  levelList=SequenceRepLevel.sent-compliance-1a-english&
  annotations=html-sent-webbedoc-default|

SentenceRepLevel sent-compliance-1a-english
  |repLevel=english&
  componentList="Recent experiments have shown that health-education material can be much more effective if it is customized for the individual reader in accordance with their medical conditions, demographic variables, personality profile, or other relevant factors."& annotations=html-sent-webbedoc-default|

Sentence sent-compliance-2
 |variations=sent-compliance-2a&
 annotations=html-sent-webbedoc-default|

SentenceVariation sent-compliance-2a
 |condition=( )&
 componentList=( )&
 levelList=SentenceRepLevel.sent-compliance-2a-english&
 annotations=html-sent-webbedoc-default|

SentenceRepLevel sent-compliance-2a-english
 |repLevel=english&
 componentList="For example, Dr Victor Strecher (now at the Comprehensive Cancer Center of the University of Michigan) and colleagues sent unsolicited leaflets to patient's of family practices on topics such as giving up smoking improving dietary behaviour, or having a mammogram."&
 annotations=html-webbedoc-default|

Sentence sent-compliance-3
 |variations=sent-compliance-3a&
 annotations=html-sent-webbedoc-default|

SentenceVariation sent-compliance-3a
 |condition=( )&
 componentList=( )&
 levelList=SentenceRepLevel.sent-compliance-3a-english&
 annotations=html-sent-webbedoc-default|

SentenceRepLevel sent-compliance-3a-english
 |repLevel=english&
 componentList="Each leaflet was 'tailored' to the recipient, on the basis of data gathered from them in an earlier survey."&
 annotations=html-sent-webbedoc-default|

Sentence sent-compliance-4
 |variations=sent-compliance-4a&
 annotations=html-sent-webbedoc-default|

SentenceVariation sent-compliance-4a
 |condition=( )&
 componentList=( )&
 levelList=SentenceRepLevel.sent-compliance-4a-english&
 annotations=html-sent-webbedoc-default|

SentenceRepLevel sent-compliance-4a-english
 |repLevel=english&
 componentList="In each study, the 'tailored' leaflets were found to have a significantly greater effect on the patients' behaviour than 'generic' leaflets had upon patients in a control group."&
 annotations=html-sent-webbedoc-default|

//The Lexicals and LexicalVariations

Lexical lexSynonyms1
 |variations=lexSynonyms1a lexSynonyms1b|&
 annotations=|

LexicalVariation lexSynonymas1a
 |condition=(role physician)&
 string="brochure"&
 value=Word.brochure&
 annotations=|

LexicalVariation lexSynonyms1b
 |condition=(not (role physician))&
 string="information"&
 value=Word.information& annotations=|

Lexical lexCompliance
 |variations=lexCompliance-a&
 annotations=|

LexicalVariation lexCompliance-a
 |condition=(role physician)&
 string="tailored health-information"&
 value=Topic.topic-compliance&
 annotations=|

Lexical lexDiabetesMaster
 |variations=lexDiabetesMaster-a&
 annotations=|

LexicalVariation lexDiabetesMaster-a
 |condition=( )&
  string="prototype"&
 value=External.external-diabetes&
 annotations=|

//The Words

Word balance
 |value="brochure"|

Word information
 |value="information"|

//The Annotations

Annotation html-doc-webbedoc-toplevel
 title="The HealthDoc Home Page"|

Annotation html-doc-webbedoc-doc-a
 |background="blue2.gif"&
 bgcolor="fffef"&
 vlink="#990099"&
 alink="#990099"&
 link="#990099"&
 title-begin="<current><font size=+4 color=\"990099\">"&
 title-end="</font></center>"&
 image-dir="/~healthdo/images/"&
 image-align="alt"&
 parent=html-doc-webbedoc-toplevel|

Annotation html-sec-webbedoc-sec1
 |title-begin="<font size=+1 color=\"990099\">"& title-end="</font>"&
 title="The goal of the HealthDoc project"&
 parent=html-doc-webbedoc-toplevel|

Annotation html-sec-webbedoc-sec 1a
 |image="businmen.jpg"&
 parent=html-sec-webbedoc-sec1|

Annotation html-sec-webbedoc-sec2
 |title-begin="<font size=+1 color=\"990099\">"&
 title-end=">/font>"&
 title="The motivation for the research"&
 parent=html-doc-webbedoc-toplevel|

//The External objects

External external-diabetes
 |fileName="diabetes.master"&
 profile=>list of parameters describing current user/audience>|

EXAMPLE 2

Customizable Health Information

```
//The parameters
PurposeParameters
    |type=insulin-dependent non-insulin-dependent&
    technical=high-technical moderate-technical low-technical&
    age=senior adult young-adult child&
    locus-of-control=doctor patient|
RepresentationalLevelParameters
    |english spl|
//The top-level object
    toplevel=Document.diabetes
//The Documents and DocumentVariations
Document diabetes
    |title="Treating Your Diabetes"&
    variations=doc.a&
    annotations=html-doc-diabetes-toplevel discourse-doc-diabetes-toplevel|
DocumentVariation doc-a
    |condition=( )&
    componentList=Section.sec1 Section.sec2 Section.sec3 Section.sec4&
    annotations=html-doc-diabetes-doc-a discourse-doc-diabetes-toplevel|
//The Sections and SectionVariations
Section sec1
    |variations=sec1 a&
    annotations=html-sec-diabetes-sec1 discourse-sec-diabetes-sec1|
SectionVariation sec1a
    |condition=( )&
    componentList=Section.subsec1-1 Section.subsec1-2&
    annotations=html-sec-diabetes-sec1a discourse-sec-diabetes-sec1|
Section subsec1-1
    |variations=subsec 1-1a&
    annotations=html-sec-diabetes-subsec 1-1 discourse-sec-diabetes-sec 1|
SectionVariation subsec 1-1a
    |condition=( )&
    componentList=Topic.topic1&
    annotations=html-sec-diabetes-subsec1-1a discourse-sec-diabetes-sec1|
Section subsec1-2
    |variations=subsec 1-2a&
    annotations=html-sec-diabetes-subsec1-2 discourse-sec-diabetes-sec 1|
SectionVariation subsec1-2a
    |condition=( )&
    componentList=Topic.topic2 Topic.topic3 Topic.topic4 Topic.topic5 Topic.topic6&
    annotations=html-sec-diabetes-subsec1-2a discourse-sec-diabetes-sec1|
//The Topics and TopicVariations
Topic topic1
    |variations=topic1a&
    annotations=html-topic-diabetes-default discourse-topic-diabetes-topic1|
Topic Variation topic1a
    |condition=( )&
    componentList=Sentence.sent1a-1 Sentence.sent1a-2&
    annotations=html-topic-diabetes-default discourse-topic-diabetes-topic1|
Topic.topic3
    |variations=topic3a topic3b&
    annotations=html-topic-diabetes-default discourse-topic-diabetes-topic3|
TopicVariation topic3a
    |condition=(type insulin-independent)&
    componentList=Sentence.sent3a-1&
    annotations=html-topic-diabetes-default decourse-topic-diabetes-topic3|
TopicVariation topic3b
    |condition=(type non-insulin-dependent)&
    componentList=Sentence.sent3b-1&
    annotations=html-topic-diabetes-default decourse-topic-diabetes-topic3
//The Sentences and Sentence Variations
Sentence sent1a-1
    |variations=sent1a-1i&
    annotations=html-sent-diabetes-default discourse-sent-diabetes-default|
SentenceVariation sent1a-1i
    |condition=( )&
    componentList=( )&
    levelList=SentenceRepLevel.sent1a-1i-english SentenceRepLevel. sent1a-1i-spl&
    annotations=html-sent-webbedoc-default|
SentenceRepLevel sent1a-1i-english
    |repLevel=english&
    componentList=Lexical.lexDiab Lexical.lexis Lexical.lexa Lexical.lexgroup Lexical.lexof Lexical.lexconds Lexical.lexin Lexical.lexwhich Lexical.lexglucose Lexical.lexlevels Lexical.lexare Lexical.lexabnormally Lexical.lexhigh.&
    annotations=html-sent-diabetes-default discourse-sent-diabetes-default|
SentenceRepLevel sent1a-1i-spl
    |repLevel=spl&
    componentList="<a Sentence Plan Language (SPL) form>"&
    annotations=html-sent-diabetes-default discourse-sent-diabetes-default|
Sentence sent3a-1
    |variations=sent3a-1i&
    annotations=html-sent-diabetes-default discourse-sent-diabetes-default|
SentenceVariation sent3a-1i
    |condition=( )&
    componentList=( )&
    levelList=SentenceRepLevel.sent3a-1i-english SentenceRepLevel.sent3a-1i-spl&
    annotations=html-sent-webbedoc-default|
SentenceRepLevel sent3a-1i-english
    |repLevel=english&
    componentList="The condition that you have is insulin-dependent diabetes."&
    annotations=html-sent-diabetes-default discourse-sent-diabetes-default|
```

```
SentenceRepLevel sent3a-1i-spl
    |repLevel=spl&
    componentList="(asc/ascription
        :tense present
        :domain (cond1/abstraction
            :lex condition
            :determiner the
            :process (have/ownership
                :lex have-possession
                :tense present
                :domain (hearer/person)
                :range cond))
        range (diab2/abstraction
            :lex diabetes
            :determiner zero
            :property-ascription (ins/quality
                :lex insulin-independent)))"&
    annotations=html-sent-diabetes-default  discourse-sent-
    diabetes-default|

//The Lexicals and LexicalVariations

Lexical lexDiab
    |variations=lexDiab-a&
    annotations=|

LexicalVariation lexDiab-a
    |condition=( )&
    string="Diabetes"&
    value=Word.Diab&
    annotations=|

Lexical lexglucose
    |variations=lexglucose-a&
    annotations=|

LexicalVariation lexglucose-a
    |condition=( )|
    string="glucose"&
    value=Word.glucose&
    annotations=|

Lexical lexhigh
    |variations=lexhihg-a&
    annotations=|

LexicalVariations lexhigh-a
    |condition-( )|
    string="high"&
    value=Word.high&
    annotations=|

//The Words

Word Diab
    |value="Diabetes"&|

Word glucose
    |value=="glucose"|

Word high
    |value=="high"&|

//The Annotations

// //HTML Annotations

Annotation html-doc-diabetes-toplevel
    |title="About Your Diabetes"|

Annotation html-doc-diabetes-doc-a
    |bgcolor="#ffffef"&
    title-begin="<h1 align=\"center\">"&title-end="
    </h1>"&
    parent=html-doc-diabetes-toplevel|

Annotation html-sec-diabetes-default
    //<default HTML markup for any Section in diabetes
        document>|

Annotation html-sec-diabetes-sec1
    |title="Basic information"&
    parent=html-sec-diabetes-default|

Annotations html-sec-diabetes-sec1a
    |title-begin="<h2 align=\"center\">"&title end="
    </h2>"&
    parent=html-sec-diabetes-sec1|

Annotation html-sec-diabetes-subsec1-1
    |title="What is diabetes?"&
    parent=html-sec-diabetes-sec1|

Annotation html-=sec-diabetes-subsec1-1a
    |section-end="<p>"&
    title-begin="<h3>"&title-end="</h3>"&
    parent=html-sec-diabetes-subsec1-1|

Annotation html-sec-diabetes, subsec1-2
    |title="The two types of diabetes"&
    parent=html-sec-diabetes-sec1|

Annotation html-sec-diabetes-subsec1-2a
    |section-end="<p>"&
    title-begin="<h3>"&tilt-end="</h3>"&
    parent=html-sec-diabetes-subsec1-2|

// //Linguistic Annotations

Annotation discourse-doc-diabetes-toplevel
    |title="About Your Diabetes"|

Annotation discourse-sec-diabetes-sec1
    |title="Basic information"&
    relations="((ord<(topic2a topic3a))
        (ord<(topic2a topic3b))
        (ord<(topic2a topic4a))
        (ord<(topic2a topic5a))
        (ord<(topic2a topic5b))
        (ord<(topic2a topic5c))
        (ord<(topic2a topic5d))
        (ord<(topic2a topic6a))
        (ord<(topic2a topic6b))
        (ord<(topic3a topic6a))
        (ord<(topic3b topic6b))
        (elaboration topic4a topic3b)
        (justification topic2a topic3a)
        (justification topic2a topic3b)
        (justification topic2a topic4a)
        (elaboration topic4a topic2a)
        (elaboration topic5a topic3a)
        (elaboration topic5b topic3b)
        (elaboration topic5c topic3a)
        (elaboration topic5d topic3b)
        (justification topic3a topic6a)
        (justification topic3b topic6b)"|

Annotation discourse-sec-diabetes-subsec1-1
    |title="What is diabetes?"&
    parent=discourse-sec-diabetes-sec1|

Annotation discourse-sec-diabetes-subsec1-2
    |title="The two types of diabetes"&
    parent=discourse-sec-diabetes-sec1|

Annotation discourse-topic-diabetes-topic3
    |corefs="((cond1 specific cond)
        (diab2 specific diab)
        (cond1 generic diab2))"&
    parent=discourse-sec-diabetes-sec1|
```

The Pseudocode
The program objects are:
BasicObject.
ResolvableObject.
DocumentObject.
DocumentObjectSet.
VariationContainer.
Variation.
Condition.
WorkingCondition.
Annotation.
External.
The Procedures
Procedures used by BasicObject classes
These procedures are used within BasicObject classes (e.g., BasicDocument, BasicSection, etc.)
Procedure: SetProperties
Parameter:
A list of property names and their corresponding values
Algorithm:
for each property in the list do set its value
Procedures used by VariationContainer classes
These procedures are used within VariationContainer classes (e.g., Document, Section, Topic), which have a list of variations. VariationContainer classes are extensions of ResolvableObject and therefore have a Resolve method.
Procedure: SetProperties
Parameter:
A list of property names and their corresponding values
Algorithm:
for each property in the list do
if property is a list of variations then set the class property "variations" to given value
else if property is a list of annotations then set the class property "annotations" to given value
else if property is defined for this class then set its value
else signal an error
end if
end for
Procedure: Resolve (for VariationContainer classes)
Parameters
(input)
An instance of WorkingCondition
(a list of purpose parameters and their current value)
(input)
An instance of List
(a list of the desired representation levels to output)
(output)
An instance of DocumentObjectSet,
i.e., a set of references to resolved DocumentObjects, with one set member for each desired level of representation of this VariationContainer instance
Algorithm:
if Resolve has already been called with this WorkingCondition then result is the previously saved result
else
call Satisfies on each variation of this Variation Container until the WorkingCondition is satisfied
call Resolve on this satisfying variation to return a DocumentObjectSet
add the appropriate annotations for this VariationContainer into the returned DocumentObjectSet
end if
if no variation satisfies the WorkingCondition then result is null
else
result is the annotated DocumentObjectSet for this VariationContainer
end if
Procedures used by Variation classes
These procedures are used within Variation classes (e.g., DocumentVariation, SectionVariation), which therefore have a selection condition.
Procedure: SetProperties
Parameters: A list of property names and their corresponding values
Algorithm:
for each property in the list do
if property is a condition then set the class property "condition" to given value
else if property is a list of annotations then set the class property "annotations" to given value
else if property is a list of components then set the class property "componentList" to given value
else if property is defined for this class then set its value
else signal an error
end if
end for
Procedure: Satisfies
Parameters:
(input)
An instance of WorkingCondition
(output)
A Boolean value
Algorithm:
if this variation satisfies the WorkingCondition then result is true
else
result is false
end if
Procedure: Resolve (for Variation classes)
Parameters:
(input)
An instance of WorkingCondition
(input)
An instance of List
(a list of the desired representation levels to output)
(output)
An instance of DocumentObjectSet,
i.e., a set of references to resolved DocumentObjects, with one set member for each desired level of representation of this Variation instance
Algorithm:
create a new DocumentObjectSet for this Variation
for each component of this Variation do
call Resolve on the current component to return a DocumentObjectSet for this component
add the appropriate annotations for this Variation into the returned DocumentObjectSet
attach the annotated DocumentObjectSet as a child of the DocumentObjectSet for this Variation
end for
result is the annotated DocumentObjectSet for this Variation
Toplevel Procedures
These are the toplevel procedures used to read in a datafile containing a master document, create instances of the document-class objects, then loop to read in new values of the purpose parameters and generate an appropriately customized version of the document, with all appropriate annotations, at each level of representation as specified by the representation-level parameters given in the datafile.

Procedure: Parse
Parameter:
Name of datafile to be read in
Algorithm:
while end-of-file has not been reached read in the next line of the datafile
if the line is a comment or a blank line then skip over it
else if the line specifies the toplevel DocumentObject then set the "toplevel" variable to reference this object
else if the line specifies the purpose parameters and their values then set the "purposeParameters" variable
else if the line specifies the possible representation levels then set the "repLevels" variable
else instantiate the specified document object
(i.e., create a new executable instance of this document-object class,
set a reference to this instance,
assign a name to this instance,
assign its properties)
end of while loop
return the reference to the toplevel DocumentObject,
the list of purpose parameters and their possible values,
the list of desired representation levels
Procedure: Reader
Algorithm:
call an application-specific interface to:
read in current values of purpose parameters
read in desired representation levels
create an instance of WorkingCondition using these values
Procedure: Main
Parameter:
Name of the input datafile
Algorithm:
call Parse
call Reader
while new purpose parameters are input
call Resolve on the toplevel object
for each specified level of representation
output the corresponding DocumentObjectSet
end for
call Reader
end of while loop The present application has been described with reference to a presently preferred embodiment. Modifications and variations of that embodiment will be apparent to a person of skill in the art. Such modifications and variants are believed to be within the scope of the present invention as defined in the claims appended hereto.

What is claimed is:

1. A computer implemented system for creating a customized document comprising a subset of a fixed set of information, said system comprising:

a) a collection of elements representing said fixed set of information, said elements being arranged hierarchically in tiers arranged in a first tier type comprising a set of elements indicating components and a second tier type interleaved therewith comprising a set of elements indicative of variations of said components, such that each element of a lower tier is connected to at least one element of a higher tier, the elements of at least one of said tiers having a set of parameters associated therewith; and b) a selection engine to receive a set of parameters associated with an intended recipient of the customized document, said selection engine being operable upon elements of said tiers sequentially form the highest tier down to apply the received parameters and thereby select a subset of said elements to form the customized document.

2. A system according to claim 1, wherein each of said variant tiers has a set of parameters associated therewith.

3. A system according to claim 2, wherein said selection engine selects one variation for each selected component, so that said parameters associated with said one selected variation are in accordance with said received parameters.

4. A system according to claim 1, wherein said elements comprise content to be included in said document by said selection engine and computer parameters to be executed by said selection engine.

5. A system according to claim 1, wherein said hierarchy comprises objects arranged in classes and said selection engine being instantiated from said elements.

6. A system according to claim 1, wherein said hierarchy provides a grammar.

7. A computer implemented method for creating a customized document comprising a subset of a fixed set of information, said method comprising the steps of:

a) establishing a collection of elements representing said fixed set information;

b) arranging said elements hierarchically in tiers arranged in a first tier type comprising a set of elements indicating components and a second tier type interleaved therewith, said second tier type comprising a set of elements indicative of variations of said components, such that each element of a lower tier is connected to at least one element of a higher tier;

c) associating a set of parameters with the elements of at least one of said tiers;

d) receiving a set of parameters associated with an intended recipient of the tailored document;

e) operating upon elements of each tier sequentially from the highest tier down to apply the received parameters and thereby select a subset of said elements comprising the tailored document.

8. A method according to claim 7, wherein each of said variant tiers has a set of parameters associated therewith.

9. A method according to claim 8, wherein said operation on each tier selects one variation for each selected component, so that said parameters associated with said one selected variation are in accordance with said received parameters.

10. A method according to claim 7, wherein said elements comprise content to be included in said document by said selection engine and computer parameters to be executed by said selection engine.

11. A method according to claim 7, wherein said hierarchy comprises objects arranged in classes, whereby said operation uses a selection engine instantiated from said elements.

12. A method according to claim 7, wherein said hierarchy provides a grammar.

* * * * *